United States Patent
Campbell et al.

(10) Patent No.: US 11,918,330 B2
(45) Date of Patent: Mar. 5, 2024

(54) HOME OCCUPANT DETECTION AND MONITORING SYSTEM

(71) Applicant: Praesidium, Inc., Washington, UT (US)

(72) Inventors: Seth Campbell, Washington, UT (US); Richard Curtis Nordgran, Springville, UT (US); Weston Brent Johnson, St. George, UT (US); Paolo Focardi, Pasadena, CA (US); Gian Franco Sacco, Pasadena, CA (US); Jim Butler, Siera Madre, CA (US)

(73) Assignee: Praesidium, Inc., Washington, UT (US)

(*) Notice: Subject to any disclaimer, the term of this patent is extended or adjusted under 35 U.S.C. 154(b) by 685 days.

(21) Appl. No.: 16/211,886

(22) Filed: Dec. 6, 2018

(65) Prior Publication Data
US 2019/0104954 A1    Apr. 11, 2019

Related U.S. Application Data

(63) Continuation-in-part of application No. 15/916,215, filed on Mar. 8, 2018, now Pat. No. 10,989,806.
(Continued)

(51) Int. Cl.
*A61B 5/024* (2006.01)
*A61B 5/00* (2006.01)
(Continued)

(52) U.S. Cl.
CPC ........ *A61B 5/02444* (2013.01); *A61B 5/0077* (2013.01); *A61B 5/0816* (2013.01);
(Continued)

(58) Field of Classification Search
CPC ........... A61B 5/00; A61B 5/0002; A61B 5/02; A61B 5/04; A61B 5/11; A61B 5/0022;
(Continued)

(56) References Cited

U.S. PATENT DOCUMENTS

| | | |
|---|---|---|
| 3,524,058 A | 8/1970 | Robertson et al. |
| 3,796,208 A | 3/1974 | Bloice |

(Continued)

FOREIGN PATENT DOCUMENTS

| | | | |
|---|---|---|---|
| CN | 202060883 U | * | 12/2011 |
| CN | 202154683 U | * | 3/2012 |

(Continued)

OTHER PUBLICATIONS

Black & Decker (48" Tower swing fan Instruction manual, Mar. 2017 (Year: 2017).*
(Continued)

*Primary Examiner* — Olumide Ajibade Akonai

(57) ABSTRACT

A occupant detection and monitoring system has a sensor unit having a radio wave transmitter, a radio wave receiver, and a wireless transmitter configured to detect and receive vital signs of an occupant; a user interface having a microcontroller, a wireless receiver configured to receive the wireless signals transmitted from the sensor unit, a means for user input, and a network card; and a means for alerting occupants and third-parties to a triggering event; wherein the microcontroller, based upon logic, activates the alerting means at the triggering event. The sensor unit may be a camera that detects the presence of an individual and register their unique heart rhythm for identification purposes. This camera can be installed at the entry points of a home, behind the counter of a business near a cash register or at a bank or any other place that desires to use surveillance as a form of security. The sensor unit may be a light bulb that comprises the components of the sensor unit. The sensor unit may be a contactless vital sign monitor capable of remotely monitoring one or more vital signs.

19 Claims, 10 Drawing Sheets

Related U.S. Application Data

(60) Provisional application No. 62/626,758, filed on Feb. 6, 2018, provisional application No. 62/595,186, filed on Dec. 6, 2017, provisional application No. 62/595,181, filed on Dec. 6, 2017, provisional application No. 62/520,258, filed on Jun. 15, 2017, provisional application No. 62/468,805, filed on Mar. 8, 2017.

(51) Int. Cl.
*A61B 5/08* (2006.01)
*G01S 13/58* (2006.01)
*G01S 13/86* (2006.01)
*G01S 13/88* (2006.01)

(52) U.S. Cl.
CPC ............ *A61B 5/746* (2013.01); *G01S 13/583* (2013.01); *G01S 13/867* (2013.01); *G01S 13/886* (2013.01); *A61B 2505/07* (2013.01); *A61B 2560/0214* (2013.01)

(58) Field of Classification Search
CPC ... A61B 5/0004; A61B 5/0205; A61B 5/0816; A61B 5/746; A61B 5/024; A61B 5/08; G01S 13/00; G01S 13/88; G01S 13/886; G01S 13/887; G01S 7/415; G01S 13/56; G01S 13/04; H04L 29/00; H04W 4/00; H04W 4/029; H04W 4/02; G16H 40/20; G16H 10/60; G16H 40/63; G06F 16/636; H04M 2250/12; H04M 2242/04; H04M 2242/30; H04M 3/5116
USPC .......................................................... 342/28
See application file for complete search history.

(56) References Cited

U.S. PATENT DOCUMENTS

| | | | |
|---|---|---|---|
| 3,875,929 A | 4/1975 | Grant | |
| 3,993,995 A | 11/1976 | Kaplan et al. | |
| 4,085,740 A | 4/1978 | Allen, Jr. | |
| 4,197,856 A | 4/1980 | Northrop | |
| 4,289,142 A | 9/1981 | Kearns | |
| 4,958,638 A | 9/1990 | Sharpe et al. | |
| 4,981,139 A * | 1/1991 | Pfohl .................... | A61B 5/0017 600/528 |
| 5,107,845 A | 4/1992 | Guern et al. | |
| 6,062,216 A | 5/2000 | Corn | |
| 6,150,941 A | 11/2000 | Geiger et al. | |
| 6,359,597 B2 | 3/2002 | Haj-Yousef | |
| 6,483,929 B1 | 11/2002 | Murakami et al. | |
| 6,583,730 B2 | 6/2003 | Lang et al. | |
| 6,693,535 B2 | 2/2004 | Van Bosch et al. | |
| 6,753,780 B2 | 6/2004 | Li | |
| 6,922,147 B1 | 7/2005 | Viksnins et al. | |
| 6,922,622 B2 | 7/2005 | Dulin et al. | |
| 7,036,390 B2 | 5/2006 | Tsuchihashi et al. | |
| 7,348,880 B2 | 3/2008 | Hules et al. | |
| 7,536,557 B2 | 5/2009 | Murakami et al. | |
| 7,868,757 B2 | 1/2011 | Radivojevic et al. | |
| 7,903,020 B2 | 3/2011 | Lin et al. | |
| 7,948,361 B2 | 5/2011 | Bennett et al. | |
| 7,956,755 B2 | 6/2011 | Lee et al. | |
| 8,031,912 B2 | 10/2011 | Dennis et al. | |
| 8,044,782 B2 | 10/2011 | Saban | |
| 8,232,874 B1 | 7/2012 | Aneiros et al. | |
| 8,428,696 B2 | 4/2013 | Foo | |
| 8,494,615 B2 | 7/2013 | Melamed et al. | |
| 8,562,526 B2 | 10/2013 | Heneghan et al. | |
| 8,611,954 B2 | 12/2013 | Gross | |
| 8,740,793 B2 | 6/2014 | Cuddihy et al. | |
| 8,781,563 B2 | 7/2014 | Foo | |
| 8,922,342 B1 | 12/2014 | Ashenfelter et al. | |
| 8,932,217 B2 * | 1/2015 | Gibson .................. | A61B 5/002 600/301 |
| 9,000,907 B1 | 4/2015 | Rembach et al. | |
| 9,184,773 B2 | 11/2015 | Nadiri et al. | |
| 9,195,799 B2 | 11/2015 | Sze et al. | |
| 9,227,484 B1 | 1/2016 | Justice et al. | |
| 9,244,021 B2 | 1/2016 | Melamed | |
| 9,451,905 B2 | 9/2016 | Buijs et al. | |
| 9,530,080 B2 | 12/2016 | Glazer | |
| 9,547,070 B2 | 1/2017 | Corcos et al. | |
| 9,552,469 B2 | 1/2017 | Jin et al. | |
| 9,553,621 B2 | 1/2017 | Nadiri et al. | |
| 9,577,992 B2 | 2/2017 | Zizi et al. | |
| 9,589,106 B2 * | 3/2017 | Bangera ................. | G16H 50/30 |
| 9,590,986 B2 | 3/2017 | Zizi et al. | |
| 9,595,143 B1 | 3/2017 | Ashenfelter et al. | |
| 9,615,765 B2 | 4/2017 | Chayat | |
| 9,625,508 B2 | 4/2017 | Chayat | |
| 9,735,899 B2 | 8/2017 | Moshe | |
| 9,813,281 B2 | 11/2017 | Nadiri et al. | |
| 9,853,976 B2 | 12/2017 | Zizi et al. | |
| 9,869,707 B2 | 1/2018 | Cohen | |
| 9,876,590 B2 | 1/2018 | Lomnitz | |
| 9,964,505 B2 | 5/2018 | Melamed | |
| 9,993,166 B1 * | 6/2018 | Johnson ................ | A61B 5/4806 |
| 10,010,253 B2 | 7/2018 | Eyal et al. | |
| 10,020,836 B2 | 7/2018 | Chayat et al. | |
| 10,041,986 B2 | 8/2018 | Nadiri et al. | |
| 10,054,096 B2 | 8/2018 | Berkson | |
| 10,056,186 B2 | 8/2018 | Rosenfeld | |
| 10,061,911 B2 | 8/2018 | Zizi et al. | |
| 10,136,853 B2 | 11/2018 | Heinrich et al. | |
| 10,153,531 B2 | 12/2018 | Chayat | |
| 10,154,422 B2 | 12/2018 | Chayat | |
| 10,182,738 B2 | 1/2019 | Melamed | |
| 10,216,905 B2 | 2/2019 | Rogers | |
| 10,398,342 B2 | 9/2019 | Tupin, Jr. | |
| 10,401,490 B2 | 9/2019 | Gillian et al. | |
| 10,410,498 B2 | 9/2019 | Coke et al. | |
| 10,492,720 B2 | 12/2019 | Phillips et al. | |
| 10,517,503 B2 | 12/2019 | Foo | |
| 10,548,476 B2 | 2/2020 | Lane et al. | |
| 10,568,565 B1 | 2/2020 | Kahn et al. | |
| 10,660,563 B2 | 5/2020 | Mcdarby et al. | |
| 10,813,809 B2 | 10/2020 | Sauser et al. | |
| 10,912,693 B2 | 2/2021 | Baker et al. | |
| 11,100,779 B1 | 8/2021 | Lin | |
| 11,114,206 B2 | 9/2021 | Coke et al. | |
| 11,241,167 B2 | 2/2022 | Vu et al. | |
| 11,253,411 B2 | 2/2022 | Sauser et al. | |
| 11,270,799 B2 | 3/2022 | DeSa et al. | |
| 2002/0057202 A1 | 5/2002 | Luzon | |
| 2003/0098784 A1 | 5/2003 | Bosch et al. | |
| 2003/0201894 A1 | 10/2003 | Li | |
| 2004/0020314 A1 | 2/2004 | Tsuchihashi et al. | |
| 2004/0056954 A1 | 3/2004 | Crandall et al. | |
| 2005/0024188 A1 | 2/2005 | Sider | |
| 2006/0025897 A1 | 2/2006 | Shostak et al. | |
| 2007/0013531 A1 | 1/2007 | Hules et al. | |
| 2009/0182204 A1 * | 7/2009 | Semler .................. | G16H 40/63 600/301 |
| 2009/0203972 A1 * | 8/2009 | Heneghan ............ | A61B 5/0816 600/301 |
| 2009/0227882 A1 * | 9/2009 | Foo ........................ | A61B 5/742 600/508 |
| 2010/0152600 A1 * | 6/2010 | Droitcour ............. | A61B 5/1113 600/534 |
| 2010/0241018 A1 | 9/2010 | Vogel | |
| 2010/0321229 A1 * | 12/2010 | Dwelly .................... | G01S 7/415 342/28 |
| 2012/0059268 A1 | 3/2012 | Tupin, Jr. | |
| 2012/0203078 A1 * | 8/2012 | Sze ........................ | G16H 40/67 600/301 |
| 2013/0001422 A1 * | 1/2013 | Lavon .................. | A61B 5/0205 250/338.1 |
| 2013/0027868 A1 * | 1/2013 | Villa-Real ............ | H01R 13/447 361/679.31 |

(56) References Cited

U.S. PATENT DOCUMENTS

| | | |
|---|---|---|
| 2013/0065641 A1* | 3/2013 | Gross .................. G08C 17/00 455/556.2 |
| 2013/0173926 A1 | 7/2013 | Morese et al. |
| 2013/0201013 A1 | 8/2013 | Schoenberg |
| 2013/0245502 A1* | 9/2013 | Lange ................ A61B 5/1102 600/595 |
| 2014/0089007 A1 | 3/2014 | Sim et al. |
| 2014/0159912 A1* | 6/2014 | Fraden ................ A61B 5/0022 340/870.02 |
| 2014/0207282 A1 | 7/2014 | Angle et al. |
| 2014/0266704 A1 | 9/2014 | Dalley, Jr. et al. |
| 2014/0276031 A1 | 9/2014 | Lomnitz et al. |
| 2015/0170503 A1 | 6/2015 | Wedig et al. |
| 2015/0185314 A1 | 7/2015 | Corcos et al. |
| 2015/0266395 A1 | 9/2015 | Bradley et al. |
| 2015/0274036 A1 | 10/2015 | Arad et al. |
| 2015/0287296 A1 | 10/2015 | Hall et al. |
| 2015/0288877 A1* | 10/2015 | Glazer ................ A61B 5/1114 348/77 |
| 2015/0311591 A1 | 10/2015 | Golombek |
| 2016/0090958 A1 | 3/2016 | Berkson |
| 2016/0167479 A1 | 6/2016 | Morin |
| 2016/0232778 A1 | 8/2016 | Honjo et al. |
| 2016/0313259 A1 | 10/2016 | Shayovitz |
| 2016/0356877 A1 | 12/2016 | Melamed et al. |
| 2017/0013069 A1 | 1/2017 | Grohman |
| 2017/0033469 A1 | 2/2017 | Hoffman et al. |
| 2017/0033808 A1 | 2/2017 | Lomnitz et al. |
| 2017/0068863 A1 | 3/2017 | Rattner et al. |
| 2017/0153324 A1 | 6/2017 | Lomnitz |
| 2017/0184647 A1 | 6/2017 | Chayat |
| 2017/0238835 A1 | 8/2017 | Melamed |
| 2018/0000408 A1 | 1/2018 | Heinrich et al. |
| 2018/0029591 A1 | 2/2018 | Lavoie |
| 2018/0050575 A1 | 2/2018 | Campbell et al. |
| 2018/0053392 A1 | 2/2018 | White et al. |
| 2018/0053393 A1 | 2/2018 | White et al. |
| 2018/0089975 A1* | 3/2018 | Amir .................. H04N 5/2252 |
| 2018/0106886 A1* | 4/2018 | Lin .................... G01S 13/88 |
| 2018/0225956 A1 | 8/2018 | Chen |
| 2018/0235542 A1 | 8/2018 | Yun et al. |
| 2019/0024350 A1 | 1/2019 | Silverstein et al. |
| 2019/0049570 A1 | 2/2019 | Xiong et al. |
| 2019/0066464 A1 | 2/2019 | Wedig et al. |
| 2019/0254544 A1 | 8/2019 | Chayat et al. |
| 2019/0279479 A1* | 9/2019 | Reunamaki .......... G08B 25/08 |
| 2020/0233079 A1 | 7/2020 | Silverstein |
| 2021/0007921 A1 | 1/2021 | Sauser et al. |

FOREIGN PATENT DOCUMENTS

| | | | |
|---|---|---|---|
| CN | 202154683 U | | 3/2012 |
| CN | 102835958 A | * | 12/2012 |
| CN | 103021118 A | | 4/2013 |
| CN | 204931636 U | * | 1/2016 |
| CN | 205068696 U | | 3/2016 |
| DE | 102009033829 A1 | | 1/2011 |
| JP | 2001183470 A | * | 7/2001 |
| JP | 2013108639 A | | 6/2013 |
| WO | 2009083017 A1 | | 7/2009 |
| WO | WO-2010004496 A1 | * | 1/2010 ......... A61B 5/02444 |
| WO | 2013155661 A1 | | 10/2013 |
| WO | 2015174879 A1 | | 11/2015 |
| WO | 2018035540 A1 | | 2/2018 |

OTHER PUBLICATIONS

Ernst, Robert et al: "60GHz vital sign radar using 3D-printed lens," 2016 IEEE Sensors, IEEE, Oct. 30, 2016 (Oct. 30, 2016), pp. 1-3, XP033037053, DOI: 10.1109/ICSENS.2016.7808774 [retrieved on Jan. 5, 2017].

Bruser, Christoph et al: "Ambient and Unobtrusive Cardiorespiratory Monitoring Techniques," IEEE Reviews in Biomedical Engineering, vol. 8, Aug. 17, 2015 (Aug. 17, 2015), pp. 30-43, XP011666728, ISSN: 1937-3333, DOI: 10.1109/RBME.2015.2414661 [retrieved on Aug. 17, 2015].

Extended European Search Report and Search Opinion for European Patent Application No. EP18887010 (dated Jul. 9, 2021).

International Search Report and the Written Opinion of the International Searching Authority, International Patent Application No. PCT/US2018/64273; dated Feb. 14, 2019.

International Search Report and Written Opinion of the International Searching Authority for PCT Application No. PCT/US2017/047870 (dated Dec. 26, 2017).

International Search Report and Written Opinion of the International Searching Authority for PCT Application No. PCT/US2018/021629 (dated Jun. 27, 2018).

International Search Report and Written Opinion of the International Searching Authority for PCT Application No. PCT/US2018/064273 (dated Feb. 14, 2019).

* cited by examiner

A. Floor Mount    C. Wall Mount    E. Stand Mount

B. Crib Mount    D. Tabletop Mount

HOME OCCUPANT DETECTION AND MONITORING SYSTEM

CROSS-REFERENCE TO RELATED APPLICATIONS

This application is a continuation-in-part of pending U.S. patent application Ser. No. 15/916,215, filed Mar. 8, 2018, which application claims the benefit of U.S. Provisional Application No. 62/468,805 filed on Mar. 8, 2017, and U.S. Provisional Application No. 62/520,258 filed on Jun. 15, 2017. In addition, this application claims the benefit of the following U.S. Provisional Application Nos.: 62/595,181 (filed Dec. 6, 2017), 62/595,186 (filed Dec. 6, 2017), and 62/626,758 (filed Feb. 6, 2018). Each of the foregoing applications are incorporated herein by reference.

TECHNICAL FIELD

The present disclosure relates to home security systems and health monitoring. More particularly, the present disclosure is directed to a system for detecting, identifying, and monitoring individuals in a home or business by using their heartbeat, respiration, or other vital signals, a camera that remotely detects the vitals of individuals, a light bulb that monitors vital statistics of occupants in a room, and a remote monitor for detecting infant vital signs.

BACKGROUND

Security and safety are major concerns for businesses and individuals. Modern home and commercial security systems are generally comprised of three primary detection methods to detect intruders: door/window sensors, motion sensors, and glass break sensors. While these technologies can be effective in some situations, they are all possible to defeat so as to miss an intruder or unwanted occupant. As an example, glass break sensors can be defeated by a glass cutter or by simply breaking a window with minimal sound; motion sensors can be defeated by crawling or otherwise keeping a low profile while moving close to walls; and door/window sensors can be overcome with the use of magnets. Other means and methods may be available to defeat these technologies. In addition to these problems, intruders can gain access to a home or business when an alarm is not activated, lying in wait until other occupants have gone to sleep or left the business. In addition, such systems require time money and time in installing and maintaining a sensor at each door, window or other potential entry point.

In addition, a major part of security is surveillance for evidence gathering as well as a deterrent of potential crime. Current cameras can capture visual evidence of an individual but can be defeated by simply wearing a mask. Many crimes are committed every year where there is insufficient evidence due to lack of a clear visual of a person's face or features or a perpetrator of a crime wearing a mask or disguise.

Therefore, there is a need for a security system that is not limited to monitoring entry points, and that can constantly monitor occupants in a home, business, or other structure to prevent an unwanted occupant from entering, or remaining, in a structure. There is also a need for a system that can accurately detect and record the vital signs of individuals for bio-identification.

Further, there are currently no systems for simultaneously monitoring the health status of each occupant within a structure. In other words, many deaths occur each year that may have been preventable, had other occupants in the home been alerted to a health emergency. For example, several children die each year from suffocation. If someone would have been alerted to the child's distress, the child might have been saved. As such, there is a need for a system that not only monitors a home for intrusion purposes, but that monitors the occupants' health statuses as well.

Accordingly, there is a need for a system capable of monitoring children or infants, in particular while the infant or child is sleeping. However, some infants and children are light sleepers and entering the room where the child is risks disturbing the sleep. Existing remote monitors may utilize microphones or video cameras to audibly or visually monitor the child, but such monitors do not capture important information such as the child's heart rate.

Other existing remote monitoring systems may monitor vital information, such as heart rate, by using a sensor that contacts the child. For example, existing monitors may use a pulse-oximeter that may be place, for example, in a sock. However, children often move during sleep and may dislodge or be disturbed by monitors that contact the child's body. Such sensors may lose contact with the child's body rendering the system incapable of monitoring. Having such contact sensors also poses a potential health hazard when positioned in an infant's crib where the monitoring equipment may pose an entanglement or choking hazard.

The ability to monitor vitals such as heart rate and respiration rate carries significant benefits. If done in a non-invasive and passive way, this could be used to alert others to cardiac and respiratory distress, collect data for health evaluations, secure a premise by notifying owners of occupants in a room, and many other applications.

The present invention seeks to solve these and other problems.

SUMMARY OF EXAMPLE EMBODIMENTS

In one embodiment, a home occupant detection and monitoring system comprises a sensor unit comprising a radio wave transmitter, a radio wave receiver, and a wireless transmitter; a user interface comprising a microcontroller, a wireless receiver configured to receive the wireless signals transmitted from the sensor unit, a means for user input, and a network card; and, a means for alerting occupants and third-parties to a triggering event; wherein the microcontroller, based upon logic, activates the alerting means at a triggering event.

In one embodiment, a home occupant detection and monitoring system further comprises one or more cameras aligned with the sensor unit, the camera configured to activate and/or record at a triggering event.

In one embodiment, a home occupant detection and monitoring system comprises a radio wave transmitter capable of transmitting Frequency Modulated Continuous Wave (FMCW) signals; one or more radio wave receivers positioned in orthogonal locations (or, in general, non-parallel locations) around an environment to be monitored; a user interface comprising a microcontroller, a wireless transceiver, a means for user input, and a network card; and, a means for alerting occupants and third-parties to a triggering event; wherein the microcontroller, based upon logic, activates the alerting means at a triggering event.

In one embodiment, a home occupant detection and monitoring system comprises a radio wave transmitter capable of transmitting FMCW, wherein the FMCW is configured to map walls of a structure by measuring distance of walls and objects with maximum return.

In one embodiment, an antenna of the radio wave transmitter, receiver, or transceiver rotates, either electronically or mechanically, to monitor an environment using narrow beam scanning (e.g., +/−45 deg.). In an alternate embodiment, the antenna would use wide (e.g., 90 deg.) beam scanning with a moveable, higher gain antenna to scan the environment for vital signals.

In one embodiment, a method of detecting occupants in a structure comprises using radar to detect one or more occupants within a structure, comparing the total number of occupants within the structure with the total number of occupants allowed in the structure as programmed by a user; and, alerting one or more individuals when the number of occupants within a structure drops below, or exceeds, a predetermined threshold.

In one embodiment, a method of detecting occupants in a structure comprises using radar to detect one or more occupants within a structure, using programmed logic to compare the radar signals with one or more stored signals, and identifying the occupants based upon the radar signals.

In one embodiment, a method of detecting, identifying, and monitoring users comprises using radar to detect one or more occupants within a structure, using programmed logic to compare the radar signals with one or more stored signals, and identifying the occupants based upon the radar signals, wherein when an irregular radar signal is received from one or more known occupants, alerting one or more occupants to the irregular radar signal received.

DETAILED DESCRIPTION OF EXAMPLE EMBODIMENTS

Figure 1:
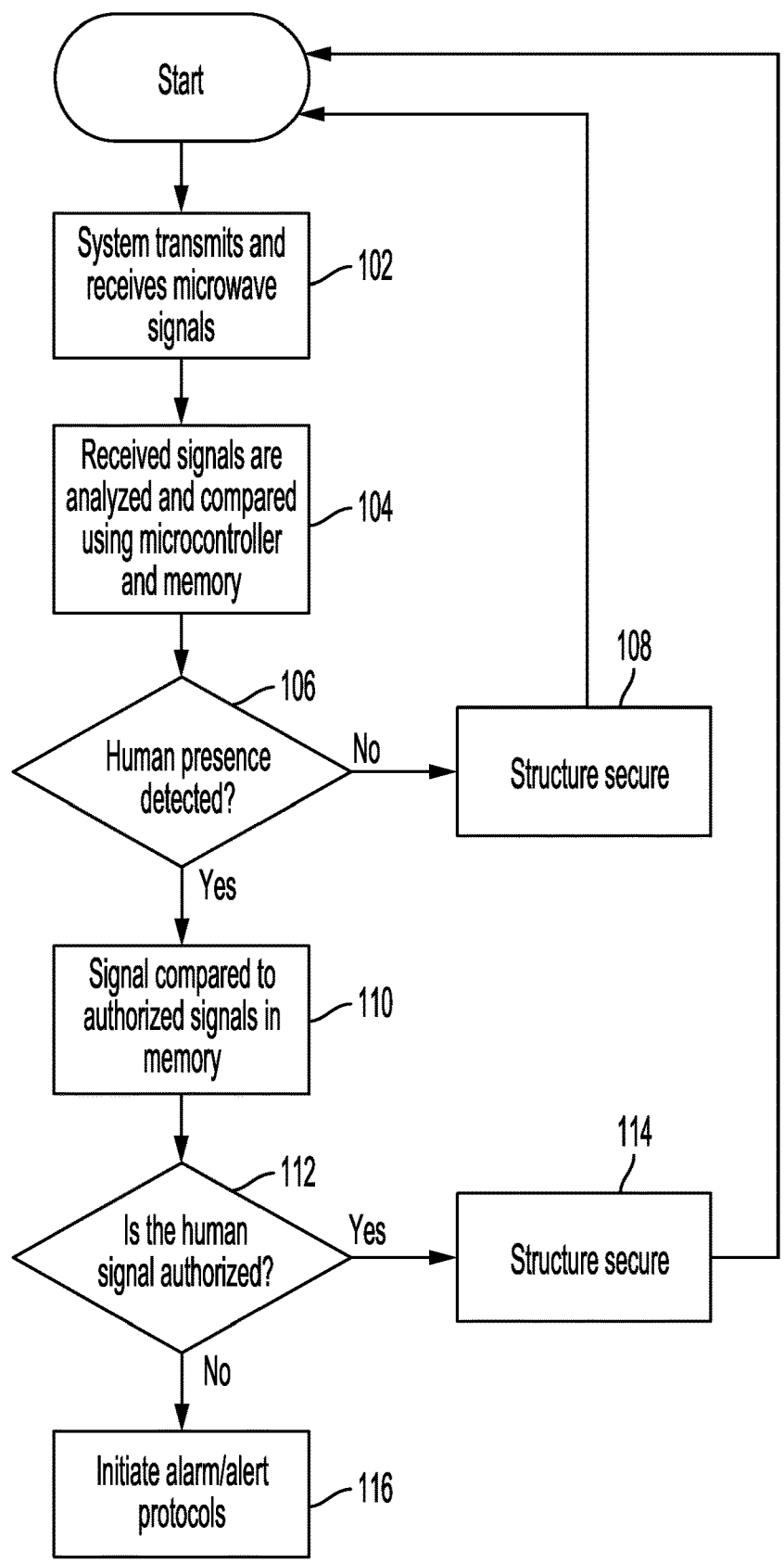
FIG. 1 is a flowchart of a home occupant detection and monitoring system.

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiment," and the like, may indicate that the embodiment(s) so described may include a particular feature, structure, or characteristic, but not every embodiment necessarily includes the particular features, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may. Further, not all drawings may be drawn to scale.

Accordingly, the particular arrangements disclosed are meant to be illustrative only and not limiting as to the scope of the invention. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed process or methods generally may be carried out in various different sequences and arrangements while still falling within the scope of the present invention.

The term "coupled" may mean that two or more elements are in direct physical or electrical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

While the term "home" may be used throughout the disclosure, the scope of the invention is not so limited. In other words, the system disclosed herein may be used in any structure or environment. Further, as used herein, an "occupant" may refer to a person or an animal.

As will be appreciated from the below disclosure, the home occupant detection and monitoring system solves the problems in the prior art—namely, the ability to monitor more than entry/exit points, and detecting the presence of an individual without the shortcomings of motion sensors. Further, the ability to monitor various health aspects of individuals within a home is an added benefit of the system disclosed herein. Some benefits of using heartbeat and breathing detection to monitor occupants include: 1) the ability to penetrate walls and concrete using radio waves so that an intruder cannot hide from detection, which would more readily detect and deter intruders from entering a premise; 2) the ability to detect when an individual has left the premise, such as a child sneaking out at night or other similar situations; and 3) the ability to monitor the health of individuals within a home or structure and potentially prevent injury or death by alerting occupants or authorities to potential health events, such as a child choking, an infant not breathing while asleep, an occupant experiencing a stroke, cardiac event, or respiratory distress, or other health event. This system disclosed herein is programmable to the specific occupants of the home and is able to alert other occupants of the home when one of the occupants is experiencing a health issue, has left the premises, or other programmable event. It also has the ability to alert the occupants to the entry of an unknown occupant.

Figure 5:
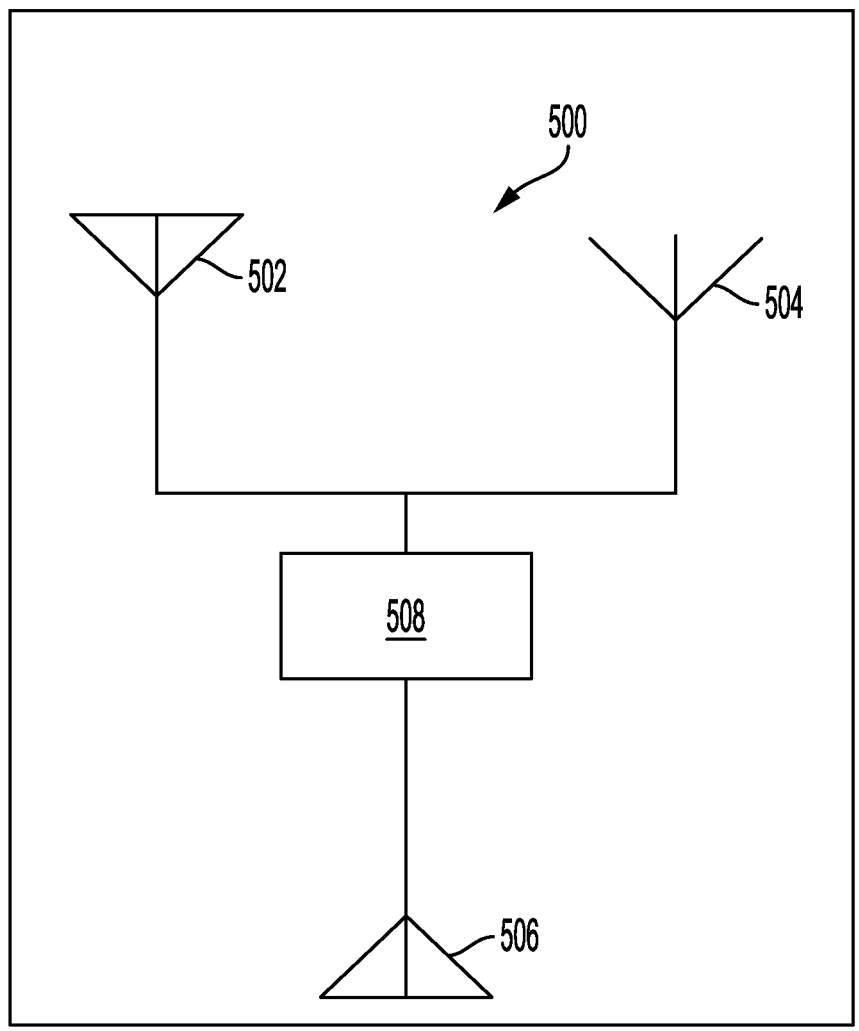
FIG. 5 is a block diagram showing components of a sensor for use with a home occupant detection and monitoring system.

In one embodiment, as illustrated by the block diagram of FIG. 5, a home occupant detection and monitoring system comprises a sensor unit 500 comprising a radio wave transmitter 502, a radio wave receiver 504, and a wireless transmitter 506. It will be appreciated that the radar components (e.g., radio wave transmitter and receiver) may comprise components known in the industry; i.e., a radar system comprises a transmitter producing electromagnetic radio waves, a transmitting antenna, a receiving antenna, and a receiver. Additionally, it will be understood that the transmitter 502 and receiver 504 may use the same antenna for transmitting and receiving. Further, the wireless transmitter may be capable of both sending and receiving signals. The sensor unit 500 may include electronic circuitry 508 as would be understood by one of ordinary skill in the art. Such circuitry 508 may include provisions for transforming, analyzing, digitizing or otherwise manipulating signals or information received by the sensor unit 500. The circuitry 508 may comprise an analog-to-digital converter, a digital-to-analog converter, memory, logic circuits or other components. The circuitry 508 may comprise individual components or one or more integrated circuit boards having one or more such components. The sensor unit(s) 500 may be placed at any number of locations, as discussed in more detail below. The transmitter 502 then transmits a radio wave signal and the receiver 504 receives the returned signal.

Figure 6:
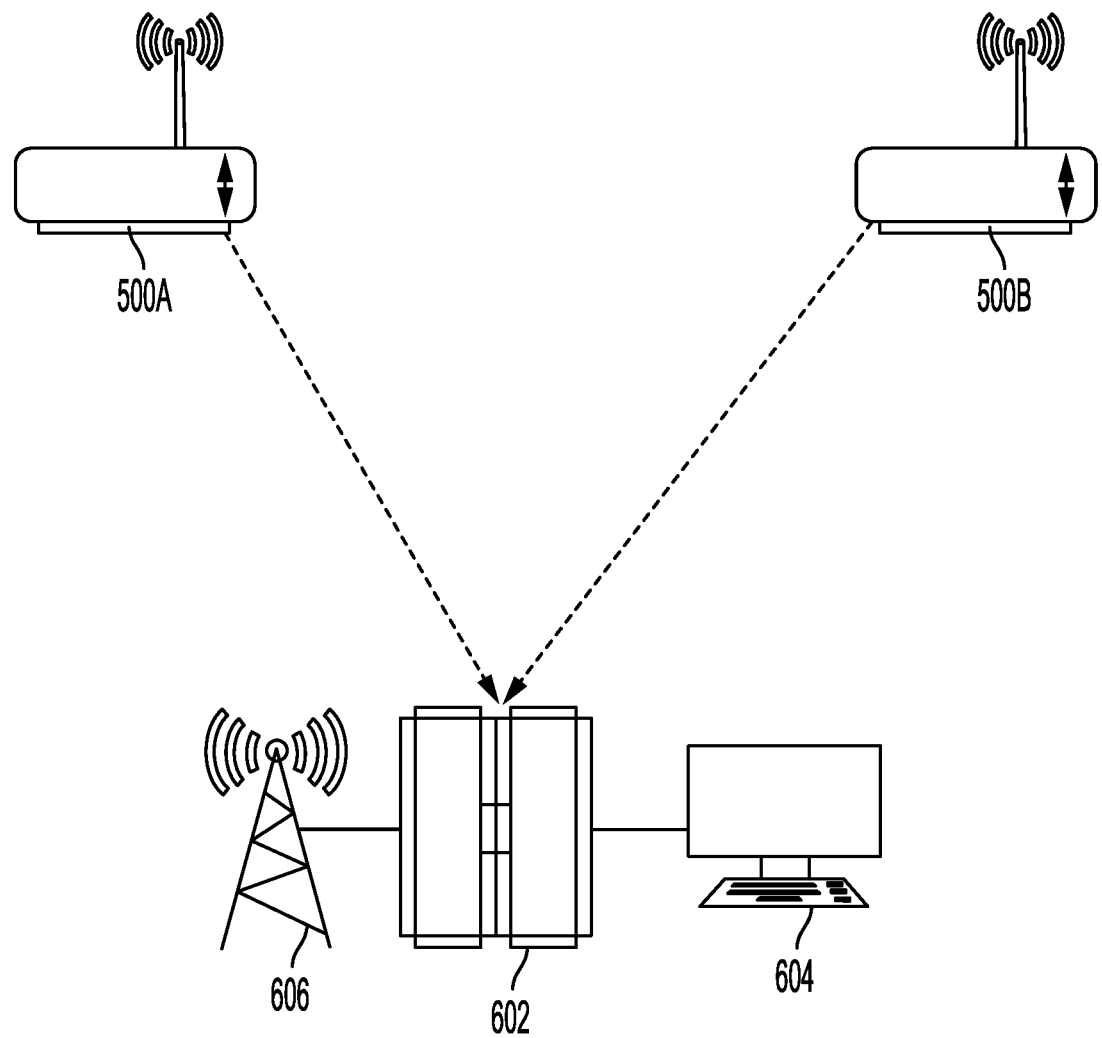
FIG. 6 is a schematic diagram of certain components of a home occupant detection and monitoring system.

As shown by the schematic diagram of FIG. 6, a monitoring system may comprise a number of elements connected into a network. The monitoring system may comprise multiple sensors 500A, 500B. While two sensors 500A, 500B are illustrated, the system may employ many more sensors distributed in a single room or in multiple rooms. As described above, the sensor transmitter 502 transmits a radio wave signal and the receiver 504 receives the returned signal. The returned signal received by the sensor 500, or a signal representative of information contained in the returned signal, is transmitted to a control unit 602 for analysis via the wireless transmitter 506. It will be appreciated that while wireless transmitters are preferred, they are not required, and wired connections may be used. Further, the network need not require the internet and may be a local area network, mesh network, or other method of communication. The control unit 602 ideally comprises a user interface, a microcontroller, a wireless receiver 606 configured to receive the wireless signals transmitted from the sensor unit 500A, 500B, a user input device, and a network communication device such as a network card (wired, wireless, or equivalent communication protocol, including, Bluetooth, ZigBee, Wi-Fi, cellular, LoRa, IR, UART, ASK, FSK and others). The user interface, microcontroller, user input device and other elements of the control unit 602 may form part of a user terminal 604. The user terminal 604 may be a personal computer, a personal electronic device such as a tablet or smartphone, including apps for such, a dedicated hardware interface, or another appropriate user interface mechanism. The user input device may be a physical device or software application, including a keyboard, a touchscreen, voice commands, or wireless connections with a smart device (e.g., smartphone app or similar). As shown in FIG. 1, the sensor unit of the system transmits a radio wave signal and then receives the signal back in step 102 (i.e., radar). The received signals are transmitted to a control unit, where, in step 104, they are analyzed using logic programmed on the microcontroller or other processor. The received signals may also be stored in memory (e.g., flash memory). The microcontroller, in step 106, is configured to identify whether a signal received is static (i.e., non-moving) or dynamic/phase varying signal (e.g., heartbeat, lungs, skin displacement, etc.). This may be accomplished using a human-determining radar application (software that is programmed to extract and compare the dynamic signal to the dynamic signals stored in memory). While the foregoing radar description is not exhaustive, an exemplary radar system is disclosed in U.S. Patent Application US20140316261A1 titled, "Life Detecting Radars" to Lux et al., which is incorporated herein by reference in its entirety. Continuing, if no human signal is present (i.e., all radio wave signals received were static), then the structure is secure (step 108). If a signal is dynamic (i.e., consistent with that of an occupant (e.g., heartbeat and/or breathing detected)), then the signal is compared in step 110 to signals stored in memory. The signals in memory were recorded at installation of the system, according to the user's desires. If in steps 112 and 114, the signal is authorized (i.e., the received signal matches a signal in memory), then the house is secure. In steps 112 and 116, if, based upon the logic, a triggering event has occurred (i.e., the received signal does not match a signal in memory), an alert is activated. Triggering events may vary according to user desire and according to the number of sensor units deployed in the house. Example triggering events are as follows: the number of heartbeats in a home drops below, or exceeds, a predetermined threshold; an unrecognized heartbeat enters the home; a known heartbeat is in the home during unauthorized hours; a known heartbeat becomes irregular; and others. The alert may comprise an alert device that provides an alert to a user of the monitoring system, including: 1) a home alarm such as an audible speaker or visually detectable indicator or light; 2) a notification to an internet connected device (e.g., smartphone, tablet, vehicle, etc.); 3) contacting emergency responders or other third-parties; and others.

A significant improvement over the prior art is the ability to monitor the home constantly, without the need to "arm" or "disarm" the system. For example, the control unit may be programmed to recognize heartbeats of specific people. This may be accomplished during an initial configuration of the system. For example, each occupant's unique heartbeat and/or breathing pattern may be read and stored in memory of the system. For example, a particular sensor may be used for a calibration mode, wherein when a heartbeat is received by the control unit from the sensor in calibration mode, an option is made available to name the received signal and set a trust level. Various trust levels may be assigned by a user, allowing the user to distinguish between occupants who live there and visitors. For example, a user may not want an alert if a known neighbor enters the home during the day (neighbor child) but would wish to be alerted if the neighbor is entering at night. As such, when the control unit analyzes the received signal and compares it with signals stored in memory, it "recognizes" each individual.

In another embodiment, rather than pre-programming neighbors, friends, and others, a control unit may be programmed to recognize familiar heartbeats based upon the number of visits to the house, and, if the user desires, the alert may be deactivated. For example, if a neighbor frequently visits the home, the homeowner, rather than formally entering the neighbor into the system, may simply set the system to not activate an alert after the fourth separate entry of the occupant (or whatever number the homeowner desires). Also, it will be appreciated that the homeowner/user can select the type of alerting means to be activated. For example, a user may select a mobile alert (e.g., text message) vs. house alarm (e.g., audible alarm using speakers) vs. contacting emergency responders, etc., depending upon the triggering event. For example, an unknown heartbeat being detected in the middle of the night may warrant more aggressive alerting means (e.g., home loudspeaker) than during the late afternoon when friends are known to visit (e.g., text message). Again, the types of alerts are selectable by a user, along with the triggering events, using programmed computer software.

Figure 4:
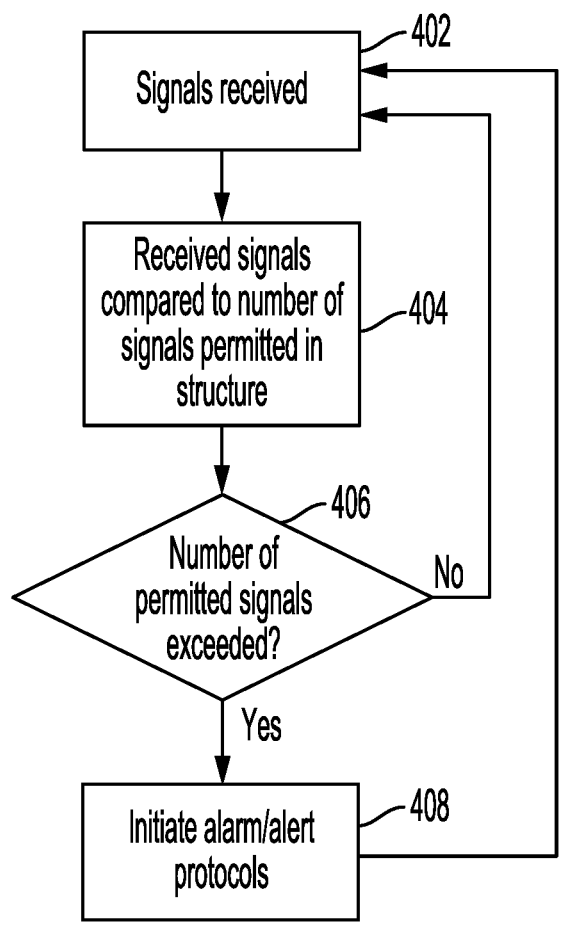
FIG. 4 is a flowchart of a home occupant detection and monitoring system.

In one embodiment, a method of detecting occupants in a structure comprises using radar (e.g., radio waves) to detect one or more occupants within a structure and compares the total number of occupants within the structure with the total number of occupants allowed in the structure, as programmed by a user. FIG. 4 illustrates a flowchart of this embodiment. As shown in step 402, radio wave signals are received by a sensor unit and are transmitted to a control unit, where, in step 404, the number of human signals (e.g., received signals that are indicative of human life, such as a heartbeat or breathing patterns, etc.) are compared against the total number of authorized individuals. In step 406, if the number of received signals do not exceed the number of allowed signals, the system loops. However, if the microcontroller concludes that the number of received signals exceeds the number authorized, an alert is initiated in step 408. For example, a user having a house with four occupants may configure the control unit to activate the alerting means if the number of heartbeats exceeds four within the structure. To prevent unwanted alerts, a user may choose a timeframe for notification (e.g., 10 pm to 7 am) or another parameter. Likewise, the system may be programmed to initiate an alert/alarm if the number of human signals received drops below a given number, which may be useful in detecting when, for example, teens are sneaking out, when a handicapped or otherwise impaired individual (e.g., Alzheimer's disease) wanders off, or other uses, as desired by a user. It will likewise be appreciated that the sensor unit may continuously transmit (e.g., continuous radio wave/FMCW) and receive signals, or may do so intermittently.

Further, the sensor unit(s) may be placed in one or more locations, depending upon the structure and the notifications desired by a user. For example, in one embodiment, a single sensor unit may be placed in the apex of an attic, where it may transmit radio wave signals downward throughout an entire house for the purpose of monitoring the entire house with a single sensor unit. However, such a system may have limitations in some configurations, such as health monitoring or undesired wandering off. For example, with a single sensor system, the control unit may not be able to adequately detect when an occupant has left the structure vs. suffered from cardiac arrest. Therefore, in another embodiment, a user may place additional sensors at thresholds so as to accurately identify who and when an occupant exits the home. For example, in a home having an Alzheimer's patient, it may be desirable to only sound an alarm when that patient exits a threshold, rather than sounding when anyone leaves. Further, there may be events when the control unit no longer detects a signal which was previously present, which has not exited through a threshold. In such a circumstance, it would be desirable to initiate an alert/alarm so that others in the house may check on the individual in case of a health problem (e.g., cardiac arrest, suffocation, etc.).

Figure 2:
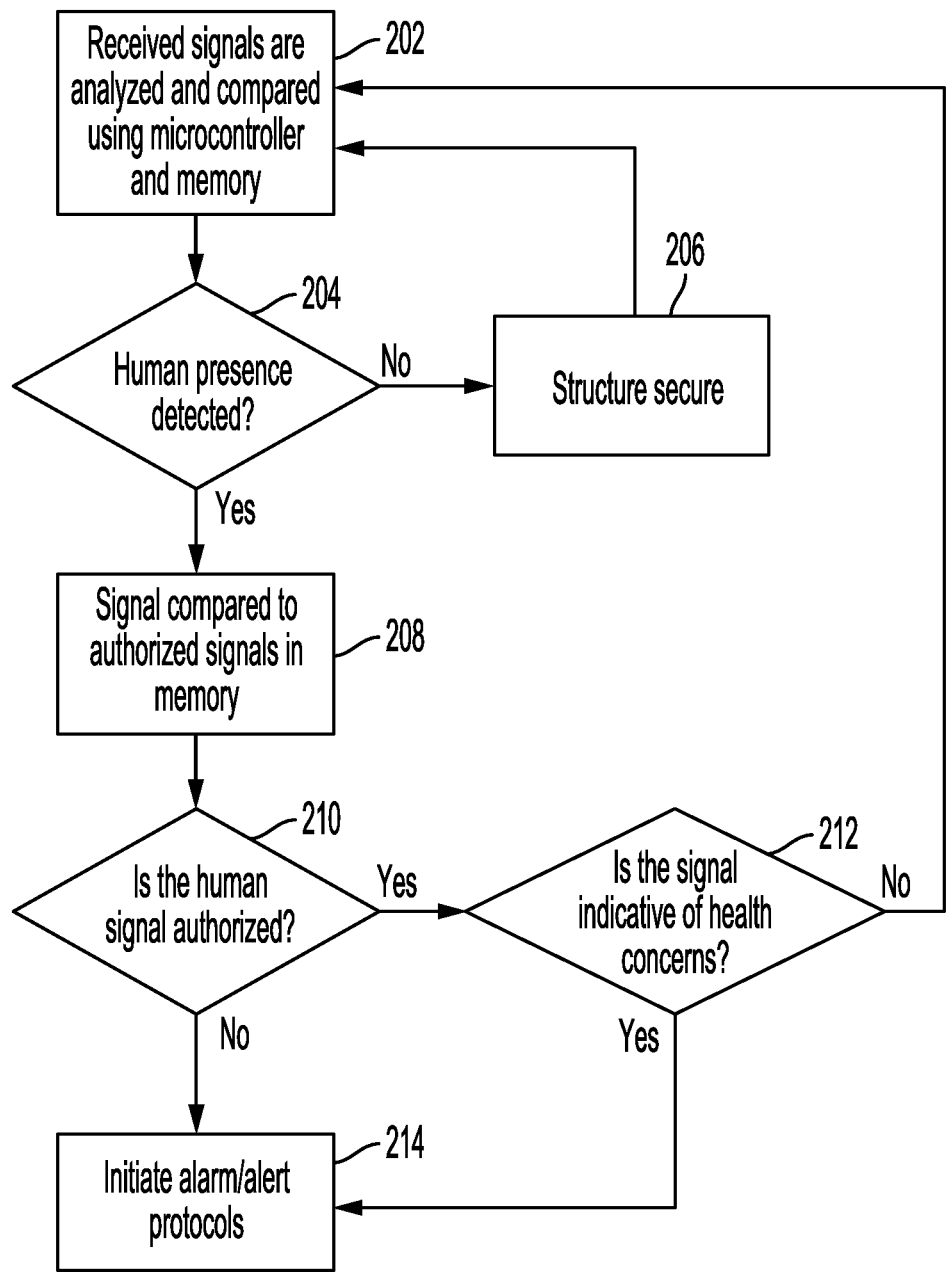
FIG. 2 is a flowchart of a home occupant detection and monitoring system.

FIG. 2 illustrates a flowchart wherein the system both verifies that the human is authorized to be in the home, and likewise compares the signal against known, previously inputted signals, to verify the health status of the individual. In step 202, received signals are analyzed and compared using a microcontroller and memory. At step 204, the system determines whether a human presence is detected. If a human presence is not detected, then at step 206 the structure is secure, and the system returns to step 202. If a human presence is detected, at step 208 the signal is compared to authorized signals in memory. After the signals are compared, the system determines whether the human signal is authorized at step 210. If the human signal is authorized, then the system determines whether the signal is indicative of health concerns at step 212. In step 212, signals indicative of health concerns (i.e., an irregular radar signal) may be when the heart rate is increased or decreased beyond a set of preprogrammed parameters (which may be known standards in healthcare or specific to an individual—which may be accomplished during calibration by taking several readings over the course of time and perhaps days, and including pre- and post-workout, etc.), when the respiration rate is outside of programmed parameters, and others. If the signal is not indicative of health concerns, the system will return to step 202. If the signal is indicative of health concerns, at step 214, the system initiates alarm/alert protocols. Returning back to step 210, if a human signal is not authorized, then at step 214 the system initiates alarm/alert protocols.

In another embodiment, a plurality of sensor units (or separate transmitter and receivers) may be used and may be placed in individual rooms for more direct readings and for the purpose of more easily identifying the location of the heartbeat. The sensor units may also be concealed behind walls, ceilings, in fixtures (e.g., appliances, light bulbs) or personal items (e.g., picture frames). For example, each sensor unit may be uniquely identifiable (e.g., MAC address, IP address, etc.) such that the control unit is able to determine which sensor unit sent the signal to the control unit. In other words, a control unit may be programmed at installation/calibration when the sensor units are installed (e.g., sensor unit "Five" is located in the "living room"). In such a scenario, the alerting means may indicate to a user not only that an unknown heartbeat has entered the structure but may also actively determine which room the stranger is located. Further, if the system is also configured to monitor health (as discussed elsewhere herein), the system may be able to identify the occupant and the location of the occupant having an emergency (e.g., respiratory distress in a child's room). Each sensor unit may be in direct communication with the control unit or may be configured in a mesh network with signals being relayed to the control unit for analysis. Further, it will be appreciated that the sensor units may be omnidirectional, unidirectional, fixed, pivotable, etc. Further, the antenna of the sensor unit may be pivotable in relation to the sensor unit.

In one embodiment, a method of detecting occupants in a structure comprises using radar to detect one or more occupants within a structure, using programmed logic to compare the received radar signals with one or more stored signals, and identifying the occupants based upon the radar signals.

Figure 3:
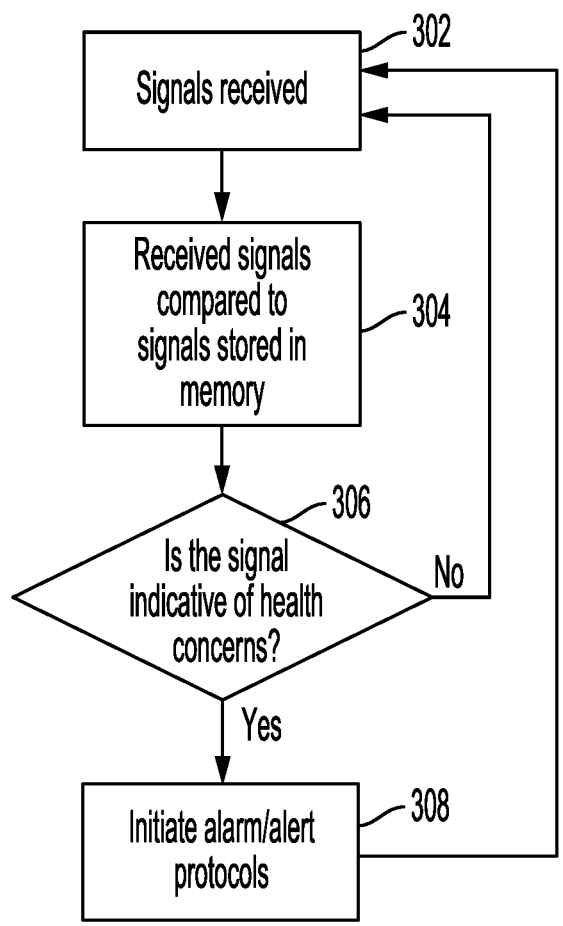
FIG. 3 is a flowchart of a home occupant detection and monitoring system.

In one embodiment, as shown in FIG. 3, the system may be used to only identify health concerns. In other words, it is not necessary for the system to be used as both security and health monitoring. A health monitoring system as shown in FIG. 3, may be well suited for care facilities, schools, or other situations where the need to monitor specific/special needs individuals is critical. In such a scenario, radar may be used to generate a signal of each individual that needs monitoring. The returned radar signal (i.e., the received signal) may then be stored in memory of the control unit. As the control unit then continues to receive signals at step 302, it compares those received signals with the signals in memory (step 304) to determine if the received signals are irregular radar signals (e.g., increased heart rate, increased respiration, etc.). At step 306, the system determines whether the received signal is indicative of health concerns. If an irregular or a signal indicative of health concerns is received, an alert/alarm is initiated in step 308. Likewise, the system may be configured to monitor thresholds to help prevent unwanted wandering off of specific/special needs individuals, which may be particularly beneficial in schools and care facilities where it may be difficult for adults to maintain constant care of individuals.

In one embodiment, a method of detecting, identifying, and monitoring users comprises using radar to detect one or more occupants within a structure, using programmed logic to compare the radar signals with one or more stored signals, and identifying the occupants based upon the radar signals, wherein when an irregular radar signal is received from one or more known occupants, alerting one or more occupants to the irregular radar signal received. Again, the alerts may take the form of phone calls, text messages or emails, third-party contact, audible house alarms or verbal information via speakers, or contacting emergency responders.

In addition to the above uses of the technology, received signals (e.g., heartbeat and respiration patterns) may be recorded/stored for additional uses, such as by law enforcement in prosecuting an individual. For example, an invader's heartbeat data would be collected and stored by the control unit. The information may then be used to verify that the correct individual has been apprehended—like fingerprint or DNA evidence is currently used. Convenience stores or other establishments may place a sensor at the threshold for the purpose of cataloging individuals. If an individual were to attempt to rob the store, the data may be used in combination with video cameras and timestamps to identify the signal of the thief. If a repeat offender, the authorities could more quickly locate the individual—no disguise would shield the would-be thief from vital sign detection. Further, if a suspect is apprehended, the radar signals may be compared for confirmation.

In one embodiment, a home occupant detection and monitoring system comprises a radio wave transmitter capable of transmitting Frequency Modulated Continuous Wave (FMCW) signals; one or more radio wave receivers positioned in orthogonal locations (or, in general, non-parallel locations) around an environment to be monitored; a user interface comprising a microcontroller, a wireless transceiver, a means for user input, and a network card; and, a means for alerting occupants and third-parties to a triggering event; wherein the microcontroller, based upon logic, activates the alerting means at a triggering event. The FMCW allows for discrimination of multiple targets at distinct distances. Further, placing the receivers (or receiving antennas) at non-parallel locations, allows for the disambiguation of subjects that may be at the same distance from one of the receivers.

In one embodiment, a home occupant detection and monitoring system comprises a radio wave transmitter capable of transmitting FMCW, wherein the FMCW is configured to map walls of a structure by measuring distance of walls and objects with maximum return. By mapping a home, a user may be presented with the map and location of subjects on the map. For example, the map and subject location may be transmitted to a user's smartphone, allowing the user to identify locations of occupants in any given structure. In one, non-limiting example, a user may transmit a signal from a smartphone to a server or other network-connected device requesting the map. The map may then be transmitted to the user, wherein occupants are displayed on the map. In another example, an alert and the map are transmitted to a user at a triggering event (i.e., home should be vacant when away on vacation, and an occupant is detected). In one embodiment, cameras may couple to the system such that a user may view the room/occupant in real-time.

In one embodiment, an antenna of the radio wave transmitter, receiver, or transceiver rotates, either electronically or mechanically, to monitor an environment using narrow beam scanning (e.g., +/−45 deg.). In an alternate embodiment, the antenna would use wide (e.g., 90 deg.) beam scanning with a moveable, higher gain antenna to scan the environment for vital signals. In other words, the higher gain antenna would continually sweep the room, detecting vital signs of occupants.

One example radar technology capable of detecting heartbeats is NASA's Finder technology. The Finder technology is a mobile system intended for locating live occupants in disaster scenarios. For example, if a building collapses as the result of an earthquake, the Finder system may be used to scan the rubble and detect any living individuals. The technology is disclosed in U.S. Patent Publication US20140316261A1 and is incorporated herein by reference in its entirety. While this system is very beneficial for that use, it is not capable of detecting occupants in a home and activating alerting means in response to triggering events.

Another technology, known as HERMA and disclosed in U.S. Patent Publication US20160048672A1, discloses the use of radio wave authentication and is also incorporated herein by reference in its entirety. That disclosure is aimed at user authentication, such as biometrics. While the above two references discuss similar technologies, which may be incorporated into the current invention, neither system discloses, or is capable of, detecting, identifying, and monitoring users in a home or other structure. As such, the present disclosure solves those problems.

In an embodiment of the invention, a life detection and bio-identification camera uses radio frequency life detection technology to detect the presence of an individual and register their unique heart rhythm for identification purposes. This camera can be installed at the entry points of a home, behind the counter of a business near a cash register or at a bank or any other place that desires to use surveillance as a form of security.

Figure 7:
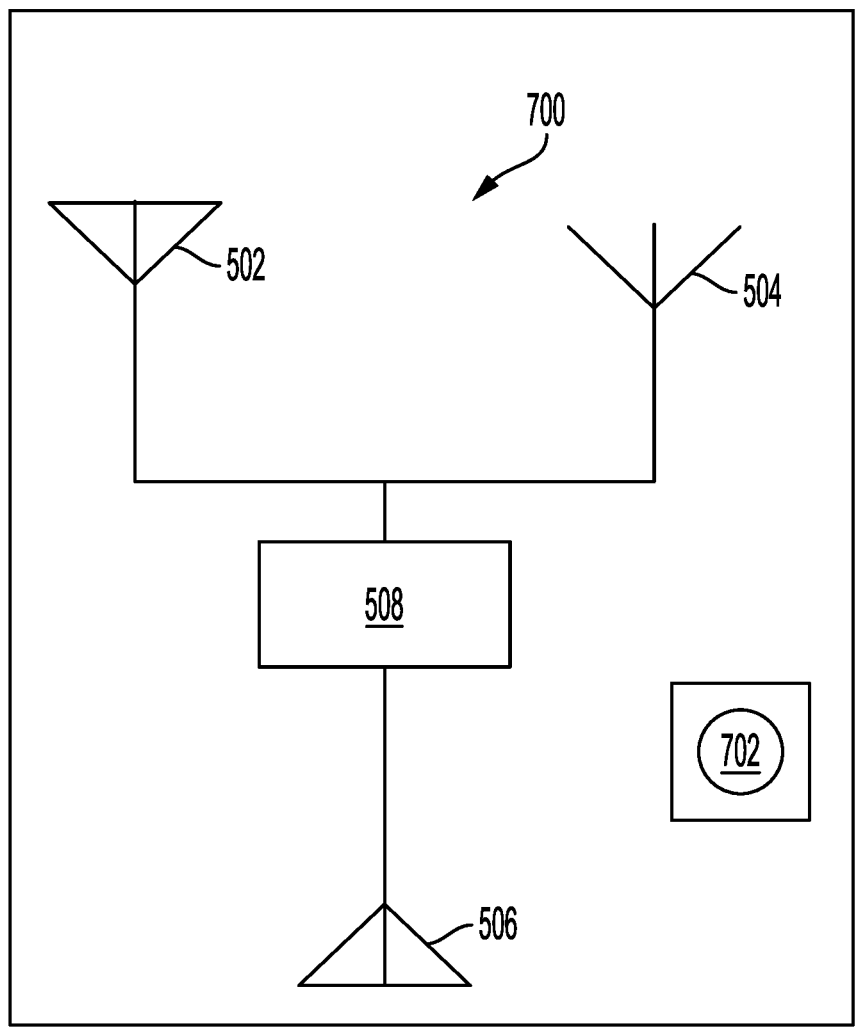
FIG. 7 is a block diagram showing components of a camera.

As illustrated in FIG. 7, embodiments of the bio identification camera 700 may include a camera module 702. The camera module may comprise a lens and appropriate circuitry to render, record, or transmit still photographs or motion video. Embodiments of the camera 700 may also contain a radio wave transmitter 502 and receiver 504. As described above, the sensor transmitter 502 transmits a radio wave signal and the receiver 504 receives the returned signal. In particular, the bio identification camera 700 may detect the motion of the heart of the subject that the camera is recording. The signal from the motion of the heart of the subject is received by an antenna in the camera. A signal processor 508 and/or microcontroller stores the unique rhythm of the heart being recorded. A software algorithm can compare the data to any future recording of the heart rhythm and be used to identify the person. Data can be transmitted wirelessly to another central processing unit or microcontroller and stored.

Embodiments of such a camera with life detection and non-contact bio-identification capabilities may further comprise a wireless transmitter 506 with the ability to communicate wirelessly with another device by means such, as but not limited to Bluetooth, Wi-Fi, cellular or any other wireless means. Embodiments may also include a remote database that receives and stores signals for analysis.

In one embodiment, the life detection and bio-identification camera system comprises a camera to capture images; a RADAR system capable of transmitting and receiving a radio frequency (RF) signal, the RF signal being processed to extract the modulation of the signal due to the displacements of the chest and body caused by the pulsations of the heart; a storage/memory device to store images and RF signals (or their encoding); and a processor to run the necessary algorithm for people identification.

Identification on images can be done using several algorithms including, but not limited to, those described in "DeepFace: Closing the Gap to Human-Level Performance in Face Verification" by Taignman, Yang, Ranzato, & Wolf, last accessed on Feb. 6, 2018 at https://www.cs.toronto.edu/~ranzato/publications/taigman_cvpr14.pdf; and "FaceNet: A Unified Embedding for Face Recognition and Clustering" by Schroff, Kalenichenko, and Philbin, last accessed on Feb. 6, 2018 at https://arxiv.org/abs/1503.03832. This publication is incorporated herein by reference.

The algorithm generates an encoding of the image. An encoding is any function applied to the raw pixels of the image and that outputs a N dimensional vector of real numbers. Identification is accomplished by defining a similarity metric which takes as input the encoding of two images and outputs a "small" number if the two images belong to the same person or a "large" number otherwise. The threshold to discriminate between "small" and "large" is a parameter of the algorithm and is set by analyzing known data. Examples of similarity metrics could be, but are not limited to, Euclidean or L2 distance, L1 or Minkowski distance, correlation etc. Sample images taken from the camera are processed by a detection algorithm with the purpose of identifying the presence of a face in the image and the bounding boxes containing the face. One example of such an algorithm can be found in "Fast YOLO: A Fast You Only Look Once System for Real-time Embedded Object Detection in Video" by Shafiee, Chywl, Li, & Wong, last accessed on Feb. 6, 2018 at https://arxiv.org/pdf/1709.05943.pdf. This reference is incorporated herein by reference. However, other algorithms could be adopted.

Identification via RF signal can be done by applying algorithms similar to those aforementioned where, in this case, the inputs are few second-long samples of the returned RADAR signal after being processed to extract the heartbeat signal.

Embodiments of a system in accordance with the present invention, may constantly sample camera frames and the returned signal of the RADAR system to perform identification. Every time an image of a face is extracted from the captured frame, the image is processed through one of the above-mentioned algorithms to check if such a face belongs to one of the subjects that are allowed on the premises by comparing the encoding of the new image with those present in the stored database of the subjects who have been granted access to the premises. A similar procedure is applied to the heartbeat signal extracted from the RADAR returned signal.

Embodiments may apply a multiple step approach to identification and notification. An identification system may first employ a method as described herein to identify a person using heart rhythm or a radar signal indicative of other information. If the initial first step fails to identify a person, the system may start recording the images captured by the camera as well as the RF signal and may take other actions, such as trigger an alarm, send notifications to a user or system manager, and/or contact law enforcement. Such correlated recordings of the camera and RF signal may be later used to positively identify the person recorded if the person is again presented to an embodiment of the camera, such as in a police line-up. Alternatively, the recording may be used to identify an individual by comparing the recording with sample recordings previously stored in a database. In this manner, an algorithm adapted for face recognition could be enhanced to identify an individual wearing a mask or other means intended to hide or camouflage their identity. Identification could trigger an alarm response, as discussed above. Alternatively, identification could trigger the system to take other actions such as locking doors, restricting access to resources, for example a safe or cash register, or any other appropriately automated response.

In a further embodiment, embodiments of a system may comprise a light bulb that contains the transmitting, receiving and processing components described above. Such a light bulb may be used to perform any or all of the functions of the various systems described above. Embodiments of the light bulb may be made as a standard bulb that can be inserted into any light fixture. This light can also be a small light that can be plugged into any standard outlet such as a night light.

Figure 8:
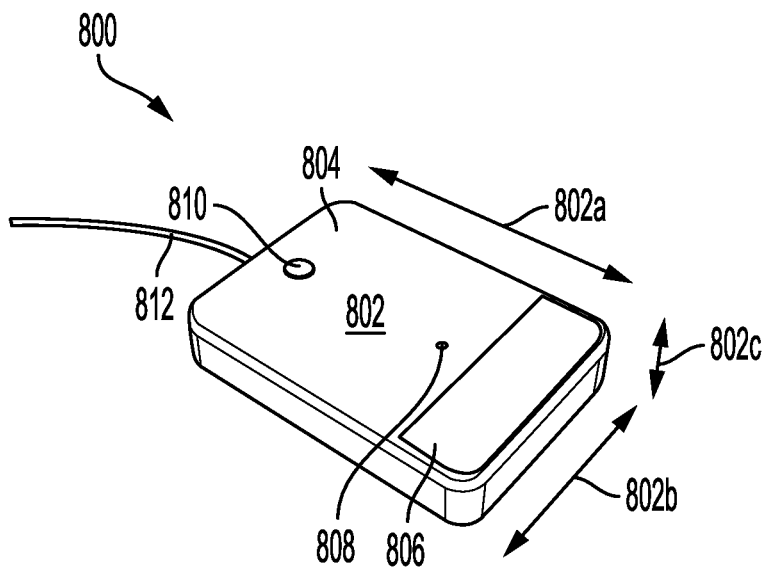
FIG. 8 is a perspective view of a contactless vital sign monitor.

Further embodiments include a contactless vital sign monitoring system. As used herein contactless means that the monitoring system does not require touching the subject being monitored or attaching or connecting any component to the subject except for the use of radio waves as described above. As such, contacting would include physical touching but does not include directing radio waves or other electromagnetic radiation at the subject. Such a monitoring system may be used to monitor vital signs of an infant or child during periods without direct supervision, such as during periods of sleep. The vital signs may include various attributes that it may be useful to monitor, including heart rate and breathing as discussed above. In addition, the monitor may include sensors or systems to monitor other vital signs, such as temperature, or other movements and activity. As illustrated in FIG. 8, vital sign monitor 800 may comprise a case 802. The case may comprise a length 802*a*, width 802*b*, and thickness 802*c*. Embodiments of the case may be configured such that the length is greater than the width, which is greater that the thickness. Further, the case may be generally rectangular and may comprise a generally flat face 804.

The face 804 of the monitor case 802 may comprise a monitoring lens 806 through which monitoring signals, as described above, are transmitted and received. The lens may be formed of an appropriate material that is transparent to the radio signals used by the monitoring system, which may include plastic or glass. The face may further comprise a power/activity indicator 808. This indicator may comprise a light, such as an LED, that emits light in one or more colors to indicate the status of the monitor, such as whether the monitor: is connected to a power source, has been turned on, is actively monitoring one or more vital signs, has triggered an alarm, or any number of other possible states. While these elements have been illustrated as positioned on the face 804 of the monitor case 802. It should be understood that they may also be positioned on other portions of the case.

The monitor 800 may further comprise a wireless communication module 810 with the ability to communicate wirelessly with another device by means such, as but not limited to Bluetooth, Wi-Fi, cellular or any other wireless means. In addition, the monitor may comprise a cable 812 extending from the case. The cable 812 may be used to provide power to the monitor. Additionally, the cable may be used to provide communications between the monitor and other devices or systems. In embodiments of the cable is a USB cable.

Figure 9:
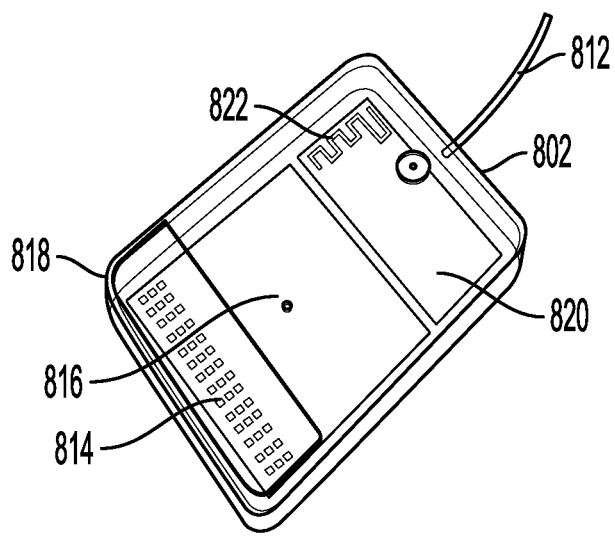
FIG. 9 is a partially cutaway perspective view of the contactless vital sign monitor of FIG. 8.

As illustrated in FIG. 9, the monitor case 802 may comprise one or more internal cavities that at least partially house various components of the monitor. Such components may include a monitoring antenna 814 that provides for sending and/or receiving the RF signal used to monitor the vital signs. The monitor may also comprise a printed circuit board 816 or other circuitry that analyzes, manipulates, records, stores or otherwise process the signals sent or received by the antenna 814.

The monitor may further comprise a battery 818. The battery may allow the monitor to function for a period of time without connection to another power source. The battery 818 may be rechargeable, and the cable 812 may provide power to recharge the battery in additions to or instead of providing power to operate the monitor. The communication module 810 of embodiments of the monitor may comprise a printed circuit board 820 containing electronic circuitry to control operation of the wireless module. The wireless module may also comprise an antenna 822 for wireless communication.

Figure 10:
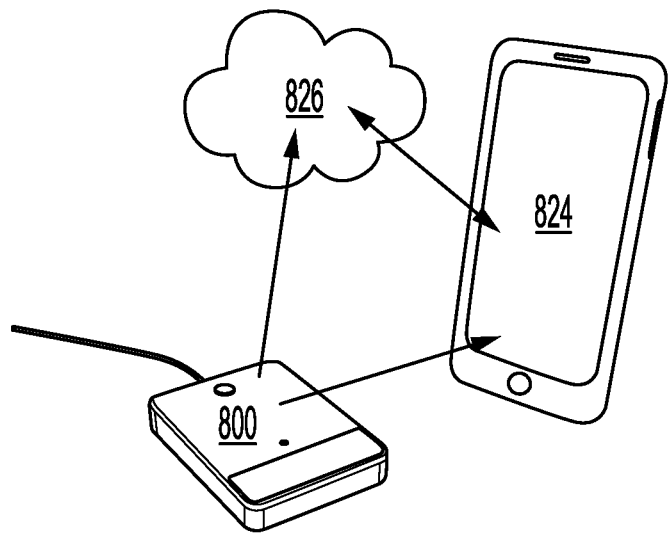
FIG. 10 is a schematic diagram of a vital sign monitoring system.

As illustrated in FIG. 10, embodiments of a contactless vital sign monitor may comprise the monitor 800. The monitor may be capable of communications with a remote receiving device 824, which may be a communication device specifically adapted to provide vital sign information in conjunction with the monitor. For example, it may be a monitor panel or station provided in conjunction with the monitor 802. Alternatively, the receiving device may be a multipurpose handheld device, such as a smartphone, mobile phone, tablet or computer. The monitoring system may comprise a software application (app) that operates on the receiving device to display information regarding one or more vital signs of the child.

The monitor 800 may communicate directly with the receiving device 824 through either a wired or wireless connection. Alternatively, the monitor 800 may communicate with the receiving device 824 by way of a network 826. The network may comprise a local area network, the Internet, or any other appropriate network using protocols that would be known to one of ordinary skill in the art. Other monitoring devices may also be connected to the monitor 800 through the network 826, and the same or different information by be sent to each of the multiple devices. For example, a first set of information may be provided to a monitoring device positioned in proximity to the child or within the same dwelling, while a second set of information, which may include less information or fewer details, is communicated to a more remote monitoring device.

Figure 11:
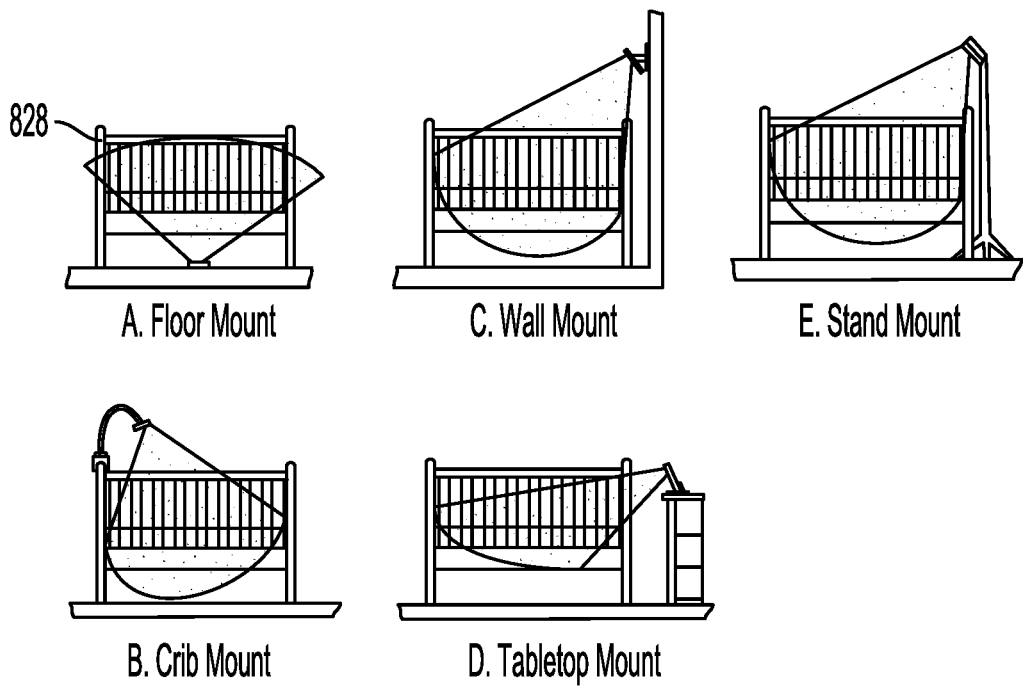
FIG. 11 illustrates a variety of potential placement positions for a contactless vital sign monitor.

As shown in illustrative embodiments A-E of FIG. 11, the monitor may be placed in a variety of different positions as long as the child is positioned within the range and path of the RF transmissions and nothing that is opaque to the RF transmissions blocks the path. For example, the monitor employs a floor mount (A) where the monitor is placed on the floor or another surface below the bed, which may be a crib 828 or other furniture supporting the child for rest or sleeping. Alternatively, the monitor may employ: a crib mount (B) where the monitor is attached to the structure of the crib or bed; a wall mount (C) where the monitor is attached to a wall or other architectural feature that is sufficiently adjacent to the crib; a tabletop mount (D) where the monitor is positioned on a table, shelf or other piece of furniture sufficiently adjacent to the crib; or a stand mount (E) where the monitor is attached to a self-supporting stand that is positioned sufficiently adjacent to the crib.

Figure 12:
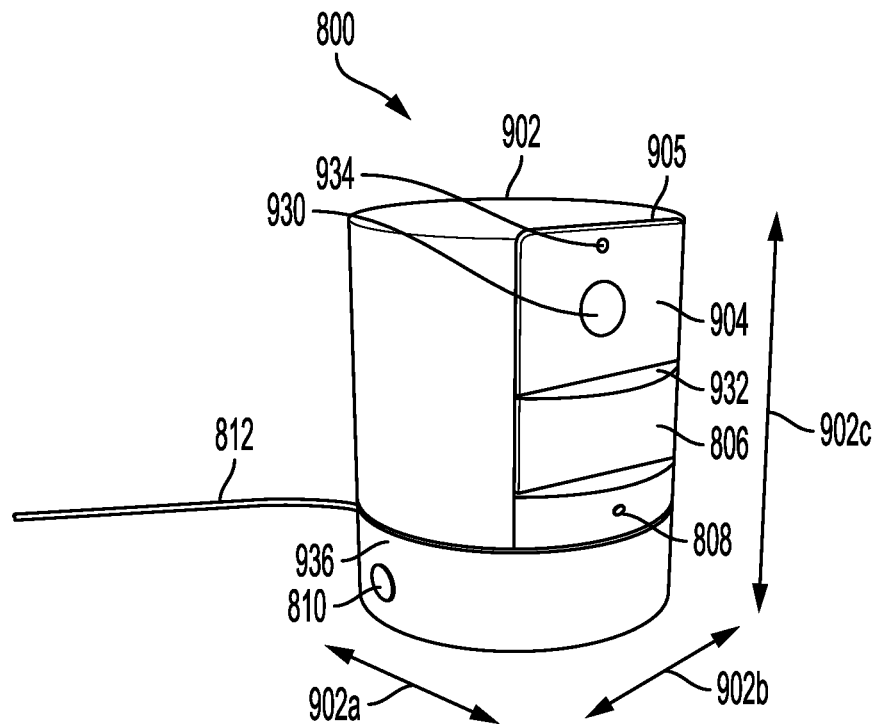
FIG. 12 is a perspective view of a contactless vital sign monitor.
Figure 13:
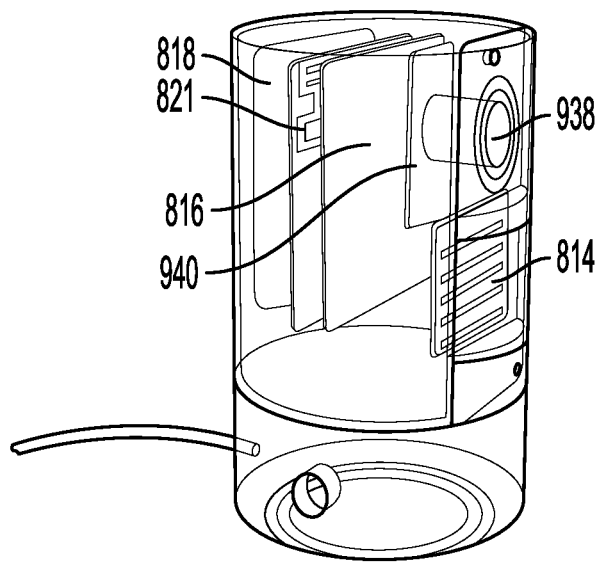
FIG. 13 is a partially cutaway perspective view of the contactless vital sign monitor of FIG. 12.

FIGS. 12-13 illustrate an alternative embodiment of the monitor 800. Vital sign monitor 800 may comprise a case 902. The case may comprise a length 902*a*, width 902*b*, and height 902*c*. Embodiments of the case may be configured such that the height is greater than the width and length such that the case extends upward from a supporting surface. Further, the case may be generally cylindrical and may comprise a generally flat face 904. However, the case may further comprise one or more covers 905 that follow the cylindrical lines of the case to maintain the general, overall cylindrical shape. Alternatively, the case may have the general shape of a truncated cone, a rectangular cuboid, a hemispherical cylinder or another shape capable of accommodating the components discussed below. In further embodiments, the face may have other shapes and may be rounded or angled, may have steps, protrusions, or subsections, or may have other nonplanar shapes or features.

The face 904 of the monitor case 902 may comprise a monitoring lens 806 through which monitoring signals, as described above, are transmitted and received. The lens may be formed of an appropriate material that is transparent to the radio signals used by the monitoring system, which may include plastic or glass. The face may further comprise a power/activity indicator 808. This indicator may comprise a light, such as an LED, that emits light in one or more colors to indicate the status of the monitor, such as whether the monitor: is connected to a power source, has been turned on, is actively monitoring one or more vital signs, has triggered an alarm, or any number of other possible states. While these elements have been illustrated as positioned on the face 904 of the monitor case 902. It should be understood that they may also be positioned on other portions of the case.

The monitor 800 may further comprise a communication module 810 with the ability to communicate with another device by means such, as but not limited to Bluetooth, Wi-Fi, cellular or any other wireless means. In addition, the monitor may comprise a cable 812 extending from the case. The cable 812 may be used to provide power to the monitor. Additionally, the cable may be used to provide communications between the monitor and other devices or systems. In embodiments of the cable is a USB cable.

In addition, the monitor may comprise other component useful in the monitoring of a child. For example, the monitor 800 may comprise a still photograph or video camera 930. A light source 934 may also be provided. The light source may be an infrared light that is not perceptible to the child but that may provide illumination that the video camera 930 is capable of perceiving. Further embodiments may comprise a microphone 932. The monitor 800 may process and transmit a combination of vital sign information together with video and audio information to provide a more complete assessment of the condition of the child.

In further embodiments, the monitor 800 may comprise a base 936 that supports the case 902 and is rotatably connected to the case. The viewing angle of the monitor may thereby be adjusted without the need to move the base. The monitor may comprise motors, gearing and circuitry that allow for remotely controlling movement of the case 902 relative to the base 936 so that the area being a monitored may be adjusted.

As illustrated in FIG. 13, the monitor case 902 may comprise one or more internal cavities that at least partially house various components of the monitor. Such components may include a monitoring antenna 814 that provides for sending and/or receiving the RF signal used to monitor the vital signs. The monitor may also comprise a printed circuit board 816 or other circuitry that analyzes, manipulates, records, stores or otherwise process the signals sent or received by the antenna 814.

The monitor may further comprise a battery 818. The battery may allow the monitor to function for a period of time without connection to another power source. The battery 818 may be rechargeable, and the cable 812 may provide power to recharge the battery in additions to or instead of providing power to operate the monitor. The communication module 810 of embodiments of the monitor may comprise a printed circuit board and antenna 821 containing electronic circuitry to control operation of the communication module and an antenna for wireless communication. The monitor may further comprise optics 938 and a printed circuit board 940 or other circuitry for the video camera 930.

In the forgoing discussion, the monitor system has been indicated as monitoring the vital signs of an infant or child. However, it should be understood that embodiments of the monitoring system could be used in any situation where contactless monitoring of vital signs would be advantageous. For example, the system may be advantageous for monitoring the vital signs of hospital patients in order to reduce the need for contact monitoring or for disturbing the patient.

Therefore, as appreciated from the above disclosure, the home occupant detection and monitoring system solves the problems in the prior art, including the ability to detect an occupant without the need of monitoring structural items (e.g., doors and windows), the ability to determine the number of occupants within a structure, their location, and their current health status, the ability accurately detect and record the vital signs of individuals for bio-identification, and the ability to monitor vital sign information of an infant or child.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention as defined in the appended claims. Additionally, it is not intended that the scope of patent protection afforded the present invention be defined by reading into any claim a limitation found herein that does not explicitly appear in the claim itself.

What is claimed is:

1. A monitor for use with a contactless monitoring system for monitoring home occupant activity, the monitor comprising:
   a face comprising:
      a lens, wherein the lens is transparent to radio waves,
      an activity indicator; and
   a case coupleable to the face comprising an internal cavity, the internal cavity comprising:
      a radio wave antenna positioned behind the lens,
      a radio wave transmitter,
      a radio wave receiver,
      a plurality of sensors,
      a memory configured to store one or more unique vital sign profiles of one or more known home occupants;
      a communication module, and
      a base rotatably coupled to the case;
   wherein the monitor uses the radio wave transmitter to transmit a radio frequency signal toward an area associated with the living subject,
   wherein the monitor uses the radio wave receiver to receive a return signal comprising a vital sign based on a detected return of the radio frequency signal, and
   wherein the monitor further forwards the return signal to a control unit that compares the vital sign to the one or more unique vital sign profiles of the one or more known home occupants, and wherein the vital sign comprises one or more of a heart rate and a respiration rate, and
   wherein when the vital sign is not recognized, based on the comparison, as belonging to the one or more unique vital sign profiles associated with the one or more known home occupants and a rate of the vital sign is above a threshold, initiate, via the control unit, an alarm.

2. The contactless monitoring system of claim 1, wherein the activity indicator comprises an LED light that emits light in one or more colors to indicate the monitor's status.

3. The contactless monitoring system of claim 1, further comprising a cable extending from the case.

4. The contactless monitoring system of claim 1, wherein vital sign is sent to a receiving device comprising a handheld communication device.

5. The contactless monitoring system of claim 4, wherein the receiving device is a mobile phone.

6. The contactless monitoring system of claim 1, wherein the communication module comprises a wireless transmitter.

7. The contactless monitoring system of claim 1, wherein the communication module comprises a second radio wave antenna positioned at least partially within the case.

8. The contactless monitoring system of claim 1, wherein the monitor further comprises a battery.

9. The contactless monitoring system of claim 8, wherein the battery is rechargeable.

10. The contactless monitoring system of claim 1, wherein the communication module simultaneously transmits information regarding the vital sign to a receiving device together with information from a video camera and information from a microphone.

11. The contactless monitoring system of claim 1, wherein the communication module transmits an alert to a receiving device upon the occurrence of a triggering event.

12. The contactless monitoring system of claim 11, wherein the triggering event is determined based upon a comparison of information regarding the vital sign to a predetermined value for the information.

13. The contactless monitoring system of claim 1, further comprising a light source comprising an infrared light.

14. The contactless monitoring system of claim 1, wherein the activity indicator comprises an LED light that emits light in one or more colors to indicate the monitor's status.

15. A monitor for use with a contactless monitoring system for monitoring home occupant activity, the monitor comprising:
   a cylindrical case comprising:
   a radio wave transmitter,
   a radio wave receiver,
   a plurality of sensors,
   a memory configured to store one or more unique vital sign profiles of one or more known home occupants, and
   a communication module,
   a face couplable to the case; and
   a base supporting the case and rotatably coupled to the case;
   wherein the monitor uses the radio wave transmitter to transmit a radio frequency signal toward an area associated with the living subject,
   wherein the monitored uses the radio wave receiver to receive a return signal comprising a vital sign based on a detected return of the radio frequency signal,
   wherein the monitor further forwards the return signal to a control unit that compares the vital sign to the one or more unique vital sign profiles of the one or more known home occupants, and wherein the vital sign comprises one or more of a hear rate and a respiration rate, and
   wherein when the vital sign is not recognized, based on the comparison, as belonging to the one or more unique vital sign profiles associated with the one or more known home occupants and a rate of the vital sign is above a threshold, initiate, via the control unit, an alarm.

16. The contactless monitoring system of claim 15, wherein the subject is a human child positioned on a bed.

17. The contactless monitoring system of claim 16, wherein the monitor is positioned below the bed.

18. The contactless monitoring system of claim 16, wherein the monitor is positioned adjacent to but not in contact with the bed.

19. The contactless monitoring system of claim 16, wherein the monitor is attached to a frame of the bed.

* * * * *